United States Patent
Pörtzgen et al.

(10) Patent No.: US 7,650,789 B2
(45) Date of Patent: Jan. 26, 2010

(54) METHOD AND APPARATUS FOR EXAMINING THE INTERIOR MATERIAL OF AN OBJECT, SUCH AS A PIPELINE OR A HUMAN BODY FROM A SURFACE OF THE OBJECT USING ULTRASOUND

(75) Inventors: Niels Pörtzgen, Vlaardingen (NL); Andries Gisolf, Delft (NL)

(73) Assignees: Rontgen Technische Dienst B.V., Rotterdam (NL); Technische Universiteit Delft, Delft (NL)

( * ) Notice: Subject to any disclaimer, the term of this patent is extended or adjusted under 35 U.S.C. 154(b) by 428 days.

(21) Appl. No.: 10/586,290

(22) PCT Filed: Jan. 14, 2005

(86) PCT No.: PCT/NL2005/000021

§ 371 (c)(1),
(2), (4) Date: May 10, 2007

(87) PCT Pub. No.: WO2005/068995

PCT Pub. Date: Jul. 28, 2005

(65) Prior Publication Data

US 2007/0277611 A1 Dec. 6, 2007

(30) Foreign Application Priority Data

Jan. 16, 2004 (NL) ................................ 1025267

(51) Int. Cl.
*G01N 29/52* (2006.01)
*A61B 8/00* (2006.01)

(52) U.S. Cl. .............................. 73/603; 73/606; 73/628; 600/447; 600/448

(58) Field of Classification Search .................... 73/603, 73/606, 624, 628; 600/437, 447, 448
See application file for complete search history.

(56) References Cited

U.S. PATENT DOCUMENTS

| 5,588,032 | A | | 12/1996 | Johnson et al. |
| 5,766,129 | A | * | 6/1998 | Mochizuki .................. 600/443 |
| 5,911,691 | A | * | 6/1999 | Mochizuki et al. ........... 600/443 |
| 6,119,089 | A | * | 9/2000 | Protopapas .................. 704/278 |
| 6,401,044 | B1 | * | 6/2002 | Ibanez Rodriguez et al. .. 702/39 |
| 7,570,742 | B2 | * | 8/2009 | Johnson et al. ............... 378/37 |
| 2009/0034756 | A1 | * | 2/2009 | Volker et al. ................. 381/119 |

FOREIGN PATENT DOCUMENTS

EP 0 829 714 3/1998

OTHER PUBLICATIONS

Langenberg, K.J., et al. "Application of modeling techniques for ultrasonic austenitic weld inspection." NDT & E International (2000) vol. 33, No. 7, pp. 465-480.

(Continued)

*Primary Examiner*—J M Saint Surin
(74) *Attorney, Agent, or Firm*—Ladas & Parry LLP

(57) ABSTRACT

A method for examining the interior material of an object, such as a pipeline or a human body, from a surface of an object using ultrasound having a frequency of at least 100 KHz, wherein the ultrasound is supplied to the interior material of the object. The reflections and/or diffractions of the ultrasound from the interior material of the object are received using ultrasonic receivers which are acoustically coupled to the surface of the object at positions which are distributed in two dimensions of the surface of the object, at different points in time or not, wherein, with each of the feelers, a receiving signal is generated, wherein the receiving signals are processed in combination in order to determine, according to the principle of inverse wave field extrapolation, where in the interior material of the object reflections and/or diffractions occur.

31 Claims, 3 Drawing Sheets

OTHER PUBLICATIONS

Javanmard, M., et al. "Inverse Problem Approach to Ultrasound Imaging." Systems, Man and Cybernetics (1995) Intelligent Systems for the $21^{st}$ Century, IEEE Int'l Conference on Vancouver, BC, Canada pp. 247-251.

Portzgen, N., et al. "Advances in Imaging of NDT Results." Proceedings of the $16^{th}$ World Conference on NDT, WCNDT (2004) Montreal, Canada [XP002311012].

* cited by examiner

METHOD AND APPARATUS FOR EXAMINING THE INTERIOR MATERIAL OF AN OBJECT, SUCH AS A PIPELINE OR A HUMAN BODY FROM A SURFACE OF THE OBJECT USING ULTRASOUND

The invention relates to a method for examining the interior material of an object, such as a pipeline or a human body, from a surface of the object using ultrasound having a frequency of at least 100 KHz, where the ultrasound is supplied to the interior material of the object.

The invention further relates to a system for examining the interior material of an object, such as a pipeline or a human body, from a surface of the object using ultrasound having a frequency of at least 100 KHz, where the system is provided with at least one transmitter for supplying the ultrasound to the interior material of the object, a plurality of ultrasonic receivers for receiving reflections and/or diffractions of the ultrasound from the interior material of the object and signal-processing means for processing receiving signals coming from the respective ultrasonic receivers.

Such a method and apparatus are known per se. For instance, the known method and apparatus are inter alia used in the non-destructive testing of a circumferential weld which connects pipelines. Such techniques have been used since around 1970. Here, the transducer (or a system of transducers) is moved over the material, with amplitude and sometimes also delay time being used for generating simple graphic displays. In those early days, a so-called facsimile recorder, the predecessor of the fax, was used for this, which was used in those days for transmitting newspaper photographs.

The technique currently used for mechanized ultrasonic examination of welds is still the same as in those days, although, the possibilities for making a graphic display have increased greatly due to the introduction of the computer. In pulse ultrasound examinations, the generated images are still composed of a series of unidimensional measurements, where either the amplitude or the delay time is translated into intensities or colors. In this manner, a computer can generate various views of, for instance, a weld. However, a disadvantage of this is that the indications shown of any deviations present in, for instance, a weld have a limited relation to the actual magnitude, shape and orientation of these deviations.

In such an examination of welds, increasingly stringent requirements are imposed on the reliability and the accuracy of the non-destructive testing used (NDT method). This is especially due to the wish to be able to trace ever smaller defects, specifically in offshore lines such as risers, which form the connection between offshore platforms and facilities on the seabed. These lines are fatigue-loaded so that a small welding flaw may already form a crack initiation which can lead to serious accidents (for instance the loss of a platform and human lives) and ecological damage. Partly for that reason, in the regulations, the acceptability criteria for welding flaws are more and more linked to fracture mechanical calculations, so that the requirements imposed on the NDT method regarding its capability of measuring the magnitude of defects once they have been detected are becoming increasingly stringent as well.

The present mechanized ultrasonic examination forms too much of a limitation to meet the future regulations. This is particularly the result of the fact that, up to now, the examination is carried out using a series of unidimensional measurements (recording of the amplitude and delay time of the ultrasonic reflections from the weld, related to reference reflectors). Using these parameters, a reasonably reliable detection and magnitude determination is only possible for certain types of defect. As a result, a priori knowledge of types, position and orientation of these welding defects is needed. The other welding defects are less reliably detected and measured.

The known method and apparatus are also used for examining a human body. One possibility is making an ultrasonic image of a fetus (ultrasound). For this purpose, the known apparatus is provided with a unidimensional array of ultrasonic transmitter and receiver elements. Each element can function both as a transmitter and a receiver. Using the ultrasonic element, a sound beam scanning in a plane is generated (a 'searchlight'). By then moving the apparatus along the body, the fetus or parts thereof can be viewed from various angles. The apparatus thus provides a two-dimensional image, namely a cross section of the fetus. The cross section corresponds with the plane in which the scanning sound beam is generated. The reflections of the beam are detected and imaged on a display. Here, a number of cross sections are imaged next to each other for obtaining a (semi) 3D representation. In this known apparatus and method, a reasonable resolution is obtained in the direction of the array while the resolution in a direction perpendicular to the array is relatively poor.

This is also, in principle, a unidimensional imaging technique, though a reasonably true-to-life image is obtained by means of filters and correlation methods.

The invention contemplates providing a method and apparatus with an improved resolution compared to the known method and apparatus.

To this end, the method according to the invention is characterized in that reflections and/or diffractions of the ultrasound from the interior material of the object are received using ultrasonic receivers which are acoustically coupled to the surface of the object at positions which are, at different points in time or not, distributed in two dimensions of the surface of the object, while a receiving signal is generated with each of the ultrasonic receivers, while the receiving signals are processed in combination to determine, according to the principle of inverse wave extrapolation, where in the interior material of the object reflections and/or diffractions of the ultrasound occur.

According to the invention, receiving signals coming from ultrasonic receivers which are distributed in two dimensions over the surface of the object are processed in combination. On the basis of the receiving signals, using inverse wave field extrapolation, the detected wave field can be traced back to the position where it came from, particularly the positions of virtual sources that arise due to reflections and/or diffractions of the ultrasound supplied to the material. In the case of an examination of a weld of a pipeline, a virtual source may be the position of a welding defect. In the case of a human body, a virtual source may be determined by the structure of the body. The receiving signals are the starting point of the inverse wave field extrapolation. On the basis of the receiving signals, the time can be mathematically inverted. With the inverse wave theory, the detected wave field is traced back to the position where it came from, namely the position of the virtual sources. The wave theory takes into account both the amplitude and the delay time of the signal. The process of tracing back the wave field measured is called the inverse wave field extrapolation. The result gives the three-dimensional positions, shape and magnitude of the virtual sources, with each shape, magnitude and position of a virtual source in effect being determined by the position of a collection of point sources from which a virtual source is made up.

Because, according to the invention, receiving signals are processed which come from ultrasonic receivers distributed in two dimensions over the surface of the object, a resolution is obtainable which is more or less equal in all directions. In addition, thus, an actual three-dimensional image of the interior material of the object can be obtained.

In the case that, in this manner, a weld of a pipeline is examined, information can be obtained about the position, shape and magnitude of a possible defect. This is because a defect forms a virtual source and accordingly a collection of virtual point sources whose positions have been determined by the position, shape and magnitude of the defect. Information can also be obtained about the nature of the defect. For instance, with a weld of a line which comprises a cavity and accordingly a defect, it can be determined whether the cavity is filled with air, liquid or copper. So, this information in effect forms a three-dimensional image of the material examined.

In particular, it holds true that the ultrasonic receivers are arranged relative to each other according to a unidimensional array, where the unidimensional array is moved along the surface in a known manner for obtaining receiving signals coming from the ultrasonic receivers distributed in two dimensions over the surface. By moving the unidimensional array along the surface, receiving signals can still be obtained which come from ultrasonic receivers distributed in two dimensions over the surface of the object.

However, it is also possible for the ultrasonic receivers to be arranged. relative to each other according to a two-dimensional array. In that case, the ultrasonic receivers do not necessarily need to be moved for obtaining a three-dimensional image.

In particular, it holds true that the ultrasound is supplied to an object such that a space comprising the interior material to be examined is completely filled with the ultrasound.

The system according to the invention is characterized in that the system is designed such that, during use, the ultrasonic receivers are acoustically coupled to the surface of the object at positions which are, at different points in time or not, distributed in two dimensions of the surface on the object, while, during use, a receiving signal is generated with each of the ultrasonic receivers, while the signal-processing means are designed to process the receiving signals coming from the ultrasonic receivers in combination according to the principle of inverse wave extrapolation in order to determine where in the interior material of the object reflections and/or diffractions of the ultrasound occur.

The invention will now be further explained with reference to the drawing, in which:

FIG. 1b shows a cross section in radial direction of the pipeline according to FIG. 1a together with the apparatus according to the invention shown in FIG. 1a;

FIG. 2b shows a cross section in radial direction of the pipeline according to FIG. 2a together with the apparatus according to FIG. 2a;

FIG. 3b shows a top plan view of a part of the apparatus of FIG. 3a in a direction of the arrow P of FIG. 3a.

Figure 1A:
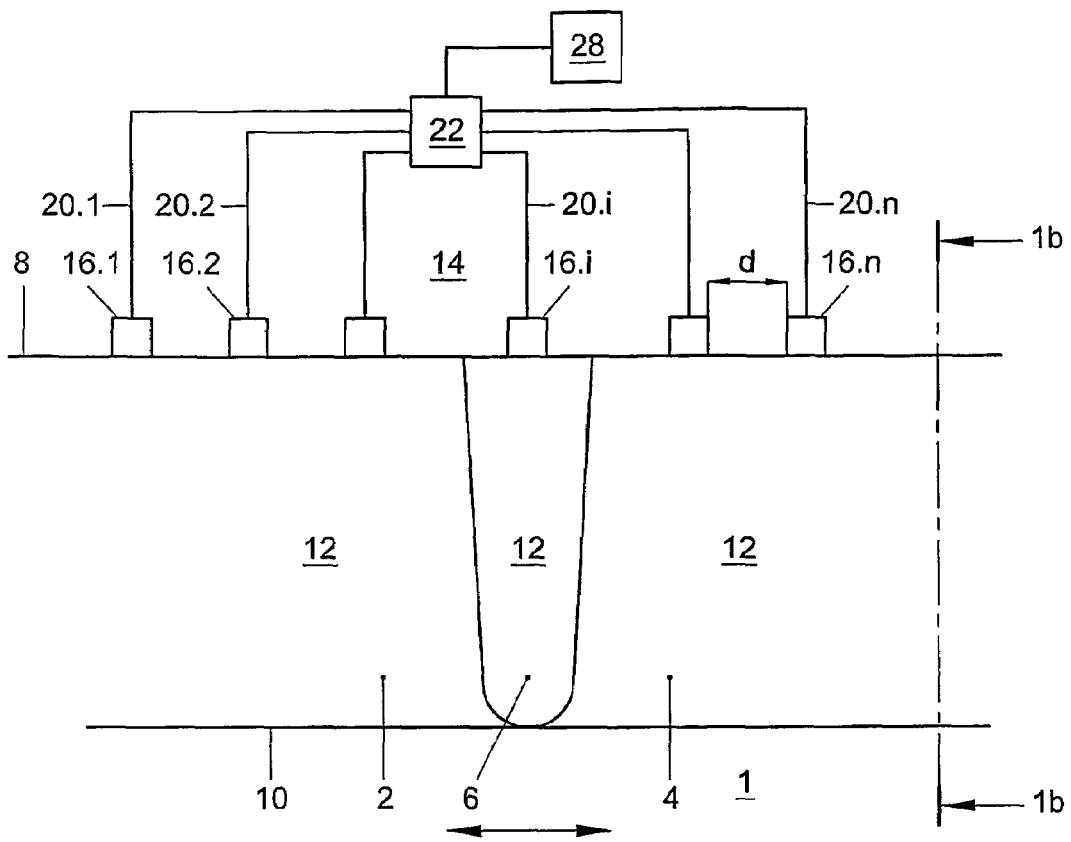
FIG. 1a shows a cross section in axial direction of two parts of a pipeline connected to each other by means of a weld and an apparatus according to the invention for carrying out a method according to the invention.

In FIG. 1a, reference numeral 1 designates an object comprising a first pipeline 2 and a second pipeline 4 and a circumferential weld 6 with which the first pipeline 2 and the second pipeline 4 are connected with each other.

Each pipeline is provided with an outer surface 8 and an inner surface 10 between which interior material 12 is present. The circumferential weld 6 is likewise provided with interior material 12.

Figure 1B:
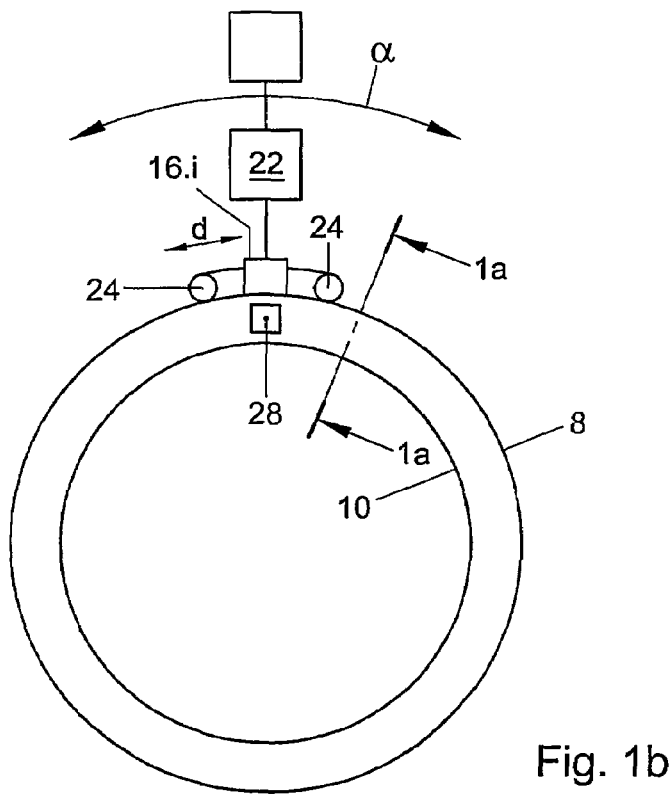

FIGS. 1a and 1b further show a system 14 for examining, from a surface of an object, in this example from the outer surface 8 of the pipelines 2, 4 and an outer surface 8 of the weld 6, the interior material 12 of the object 1, particularly that part of the object that comprises the weld 6. The system 14 is provided with a number of ultrasonic receivers 16.i (i=1, 2, 3, ..., n) arranged relative to each other according to a unidimensional array. This array extends in axial direction of the pipelines 2, 4. Here, the number n is a natural number greater than or equal to 2. A practical value is for instance n=36. The system is further provided with at least one transmitter for supplying ultrasound to the interior material 12 to be examined. In this example, each ultrasonic receiver 16.i is also designed as an ultrasonic transmitter 16.i. The ultrasonic transmitter and receiver elements 16.i, herein also referred to as ultrasonic feelers 16.i, are connected with signal-processing means 22 via respective lines 20.i. The system 14 is further provided with transport means 24 known per se, which are diagrammatically indicated in FIG. 1b, to move the unidimensional array of ultrasonic transmitter and receiver elements 16.i in radial direction around the object 1.

The operation of the system is as follows. Using, for instance, all ultrasonic transmitter and receiver elements 16.i, ultrasound is supplied to the interior material 12 of the object 1 in a pulsed manner. For this purpose, the ultrasonic transmitter and receiver elements are acoustically coupled to the interior material. In practice, this can be realized by applying a liquid film to the outer surface of the object, while the ultrasonic transmitter and receiver elements are placed so as to abut the surface of the object 1. The ultrasound supplied has a frequency higher than 100 KHz. The transmission of the ultrasound is controlled by the signal-processing means 22, such that, in this example, the ultrasonic transmitter and receiver elements 16.i transmit simultaneously at a pulse repeat frequency which is, for instance, higher than 25 Hz. The ultrasound will propagate through the material of the object 1 and reflection and/or diffraction will occur when the sound passes or hits a transition in the material (such as walls and/or welding flaws). Such a reflection and/or diffraction can be taken as a new virtual source whose sound energy in turn propagates through the material. With the unidimensional array of ultrasonic transmitter and receiver elements 16.i, the ultrasound coming from the "new virtual sources" is in turn received. Each virtual source consists of a collection of point sources whose positions can be determined. Therewith, the position, magnitude and shape of the respective virtual source can also be determined. Thus, each ultrasonic receiver 16.i generates a receiving signal which is supplied to the signal-processing means 22. The received ultrasonic signals are recorded during a certain period. This period is, for instance, chosen such that a virtual source located in the interior material 12 at a maximum distance from the ultrasonic transmitter and receiver elements 16.i is still received before a next ultrasound pulse is supplied to the interior material of the object. This may, for instance, be a defect in the weld 6 located near the inner surface 10 of the pipelines 2,4. It may also be a defect located between the weld and one of the pipelines near the inner surface 10. This is because the ultrasound first needs to propagate from the ultrasonic transmitter and receiver elements 16.i to the respective flaw and then propagate back from the flaw to the ultrasonic transmitter and receiver elements 16.i due to diffraction and/or reflection of the sound as a result of the flaw.

Further, the ultrasonic receivers 16.i are moved in the direction of the arrow 26 using the means 24. The speed of the movement may for instance be such that, between the transmissions of two ultrasonic pulses, the linear array is moved over a distance equal to the distance between adjacent ultrasonic receivers of the linear array. However, other, for instance smaller, distances are also possible. One possibility is a distance of a few millimeters where the distance between adjacent receivers of the array is a few centimeters. All this means that, in this example, when the linear array has been moved over a distance d, again a pulse of ultrasound is supplied to the interior of the body of the object 1. Completely analogously, using each of the ultrasonic receivers 16.i, a receiving signal is generated which is supplied to the signal-processing means 22. So, the ultrasonic feelers are acoustically coupled to the outer surface of the object at positions which are, in this example at different times, distributed in two dimensions of the surface of the object for generating receiving signals. That, in this example, the respective positions are distributed in two dimensions of the surface of the object at different times and not at one point in time, is, on the one hand, the result of the receivers 16.i being arranged relative to each other according to a unidimensional array and, on the other hand, the result of the receivers being moved as discussed hereinabove. Were the receivers 16.i not moved, then the respective positions would be distributed in one dimension of the surface not only at one point in time but at different times.

The receiving signals coming from the receivers which are distributed in two dimensions of the surface are processed in combination in order to determine, according to the principle of the inverse wave field extrapolation, where in the interior material 12 of the object 1 reflections and/or diffractions of the ultrasound occur. The result gives the positions of the above-mentioned virtual sources. In the case that a weld of a pipeline is examined in this manner, information can be obtained about the position, shape and magnitude of a possible defect. This is because a defect forms a virtual source and accordingly a collection of virtual point sources whose positions are determined by the position, shape and magnitude of the defect. So, this information in effect forms a three-dimensional image of the material examined. Further, information can be obtained about the nature of the defect. For instance, of a weld of a line comprising a cavity and accordingly a defect, it can be determined whether the cavity is filled with air, liquid or copper.

On the basis of the receiving signals the time can be mathematically inverted. With the wave theory, the detected wave field is traced back to the position where it came from, namely the position of the virtual sources. In this example, these virtual sources may, for instance, be welding defects. The wave theory takes into account both the amplitude and the delay time of the signal. The process of tracing back the measured wave field is called inverse wave field extrapolation and is known per se.

If the signals of the unidimensional array of receivers were only processed when the receivers are at one single position, a reasonable resolution in axial direction would be obtained. In axial direction, the unidimensional array in effect functions as a lens which makes a "sharp" image in axial direction. However, in radial direction, the resolution is relatively poor. By now also processing receiving signals from ultrasonic receivers displaced relative to each other in radial direction, the resolution in radial direction can be improved. Then, the "effect of a lens" is also present in that direction. The result is that, with the signal-processing means 22, magnitude, position and even the shape of a virtual source and accordingly the magnitude, position, shape and nature of, for instance, defects in the weld of the object 1 can be detected. More in general, the position, shape, magnitude and nature of "irregularities" in the interior material can be determined.

If it is intended to analyze, for instance, a space 28 which comprises a part of the interior material 12 and in effect forms a subspace of the object 1, the ultrasound is supplied to the object such that this space is preferably completely filled with ultrasound. Further, the linear array is moved over, for instance, an axial angle $\alpha$ (see FIG. 1b) along the outer surface of the pipelines during the transmission of the pulsed ultrasound. When the receiving signals from the unidimensional array, which have been generated during the moving of the unidimensional array over the angle $\alpha$, are processed in combination, the interior material of the space 28 can thus be examined well. Here, it is not necessary for the unidimensional array to be moved over an angle of 360 degrees around the pipelines 2,4. Because, in this example, receiving signals corresponding to ultrasonic signals transmitted at different moments are processed in combination, this involves processing different physical experiments in combination.

In this example, the receiving signals are processed in real time. The processing of the receiving signals is carried out such that the result of the processing can be imaged on a display. For this purpose, the apparatus is, in this example, provided with a display 28. Now the position, magnitude, shape and nature of each virtual source are known, the information obtained about the virtual sources can be imaged on the display in various manners. For instance an, in perspective, three-dimensional image of the interior material can be made. Here, one looks through the object from outside, as it were. However, it is also possible to have the point of view from which the material is imaged inside the material. The point of view and the direction of view may then be chosen by an operator, for instance using a joystick. One travels through the material, looking around, as it were. Such variants are understood to be within the framework of the invention. However, the receiving signals may also be saved in order to be processed later.

Figure 2A:
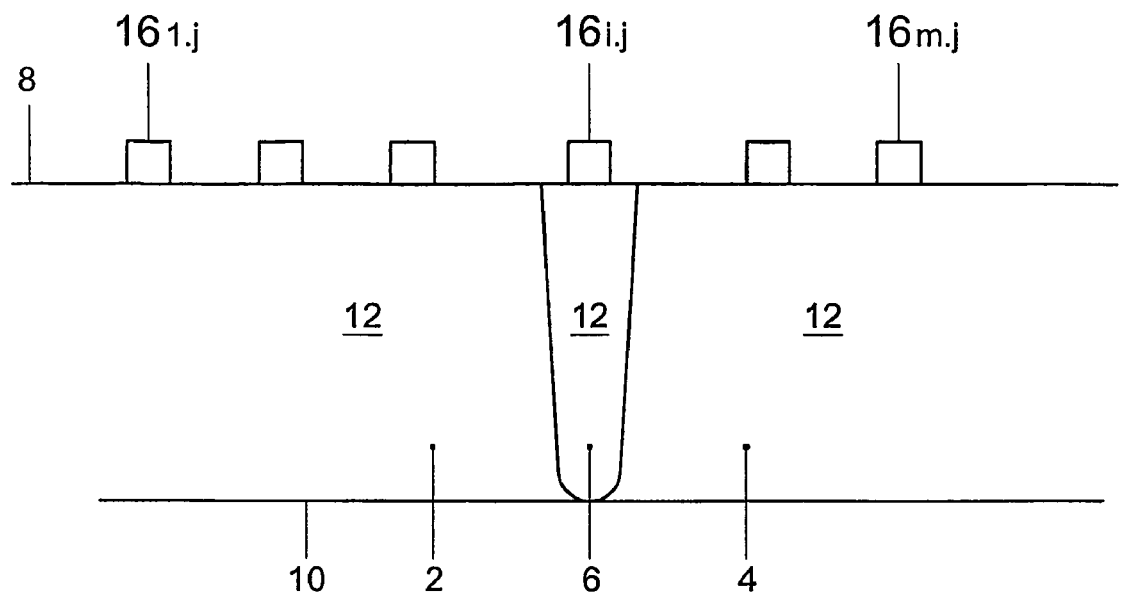
FIG. 2a shows a cross section in axial direction of two parts of a pipeline connected to each other by means of a weld, and a second embodiment of an apparatus according to the invention for carrying out a method according to the invention.
Figure 2B:
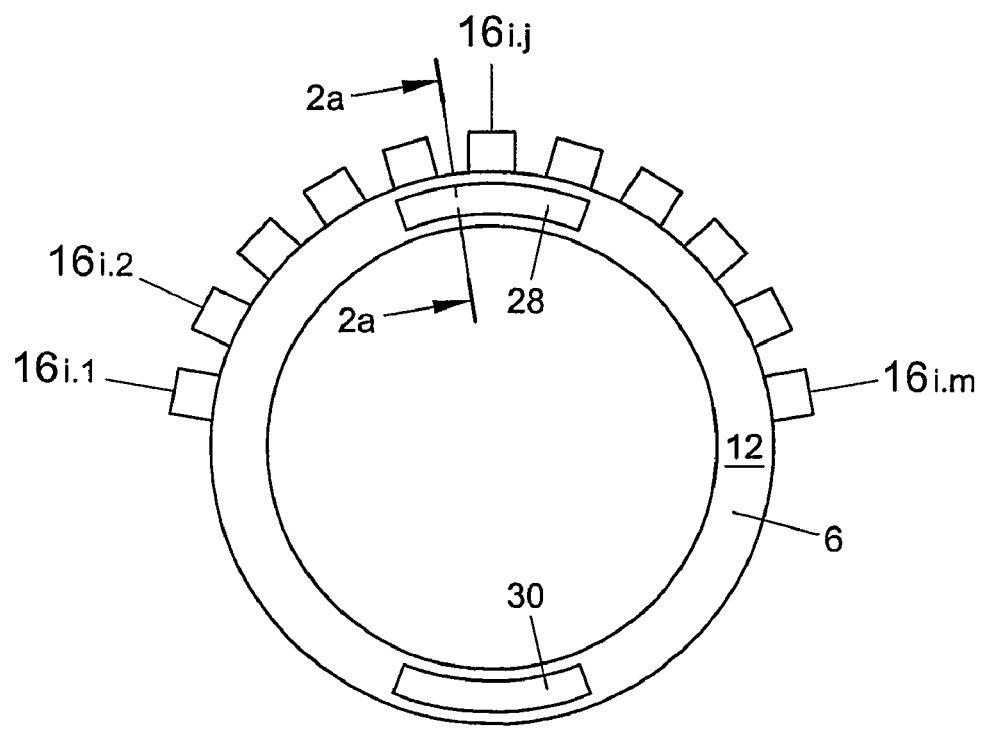

According to an alternative embodiment of the invention, it holds true that the ultrasonic feelers are arranged relative to each other according to a two-dimensional array. All this is shown in FIGS. 2a and 2b. The apparatus according to FIGS. 2a and 2b is provided with a two-dimensional array of ultrasonic receivers (16.i.j. (i=1, 2, 3, . . . , n; j=1, 2, 3 . . . , m). Here, it holds true that n and m are greater than or equal to two. Because now a two-dimensional array of ultrasonic receivers is present which are, in this case, distributed in two dimensions of the outer surface of the object at one and the same time, the ultrasonic receivers need not be moved along the surface now for obtaining receiving signals which can be processed in combination according to the principle of inverse wave field extrapolation as discussed hereinabove. In this example, each ultrasonic receiver 16.i.j. is also designed as an ultrasonic transmitter 16.i.j. Completely analogous to what has been discussed for FIG. 1, all transmitters generate, for instance, a pulsed ultrasonic signal simultaneously (in phase). This involves one physical experiment. Of each pulse, diffractions and/or reflections of the ultrasonic signal at transitions in the material are measured using the ultrasonic receiver 16.i.j., while each ultrasonic receiver 16.i.j. generates a receiving signal which is supplied to the signal-processing means for determining, according to the principle of inverse wave field extrapolation, where in the interior of the material reflections and/or diffractions of the ultrasound occur. As said, these reflections and/or diffractions can be caused by transitions in structure or density in the interior material 12. In the case of metal pipelines, these may be transitions between different grid structures of the material, a transition between different types of material, and, with the weld 6, defects of the weld. A defect may, for instance, comprise a space between weld and pipeline which is not filled with welding material and therefore forms a transition in the interior of the material which will cause diffraction and/or reflection of the ultrasound. This "hollow space" in the material will then behave like a virtual source as discussed hereinabove.

In the apparatus according to FIG. 2a, for examining for instance a space 28, it is not necessary that the two-dimensional array of receivers 16.i.j. moves along the outer surface. If one wishes to examine, for instance, area 30 in addition to area 28, then, the two-dimensional array can be moved to the area 30 if desired. So, in the case that a two-dimensional array is used for a pipeline, it is not necessary to surround the whole pipeline using ultrasonic receivers 16.i.j. What is sufficient is, for instance, providing ultrasonic receivers distributed over a radial angle smaller than 360 degrees, preferably about 180 degrees. Of course, this does not exclude the possibility that the ultrasonic receivers are provided over a radial angle of 360 degrees around the pipeline and the weld. In that case, the whole circumferential weld can be examined in one go.

Figure 3A:
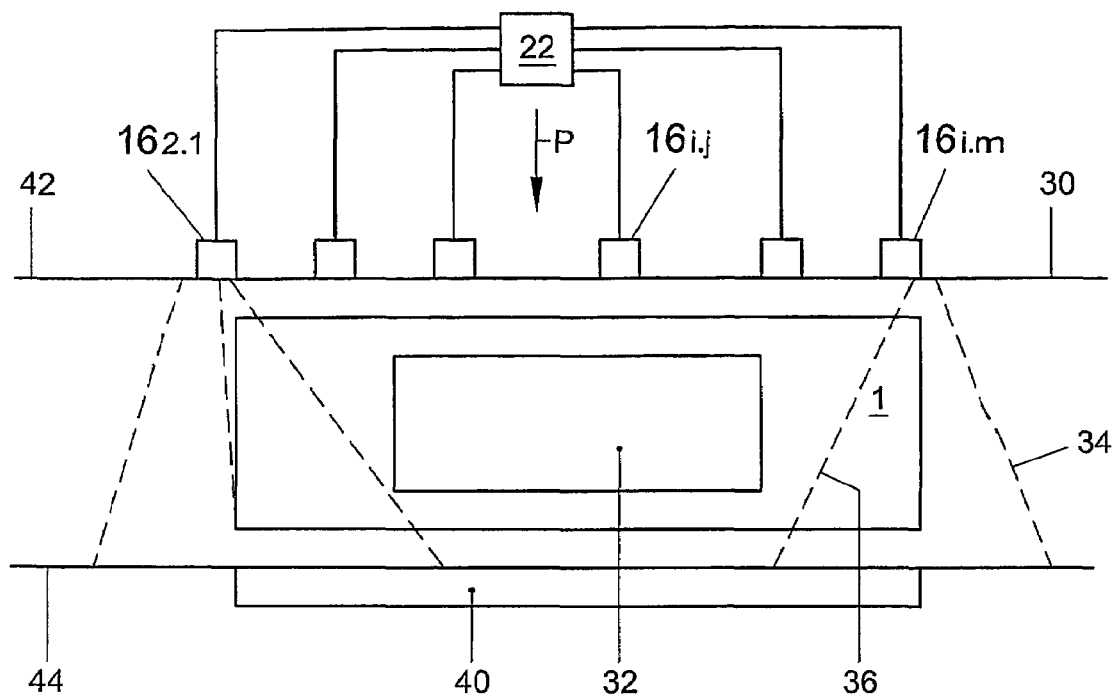
FIG. 3a shows a side elevational view of a part of a human body together with a third embodiment of the apparatus according to the invention for carrying out a method according to the invention.
Figure 3B:
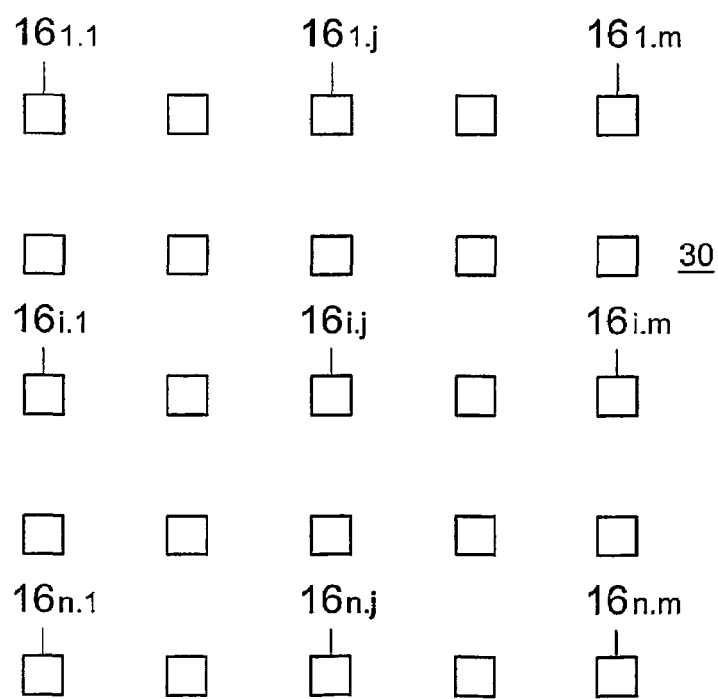

In FIG. 3, an alternative embodiment is shown of a system according to the invention for carrying out a method according to the invention. Here, parts corresponding with FIGS. 1 and 2 are designated by the same reference numerals. The object examined in FIG. 3a is a human body 1. It holds true for the apparatus according to FIG. 3a as well that the ultrasonic receivers 16.i.j. can each also function as ultrasonic transmitters 16.i.j. In this example, the ultrasonic transmitter and receiver elements 16.i.j. are in rows and columns, and are arranged relative to each other in an at least virtually flat plane 30. Completely analogous to what has been discussed hereinabove, using each of the ultrasonic transmitters 16.i.j., a pulsed ultrasonic signal is transmitted simultaneously (in phase), which propagates through the interior material 1 of the body. After the sound has been transmitted, reflections and/or diffractions of the ultrasound in the interior material are received using the ultrasonic receivers 16.i.j. Each of the receiving signals generated using the ultrasonic receivers 16.i.j. is supplied to the signal-processing means 22, where the position of the virtual (point) sources in the material can be calculated using inverse wave field extrapolation so that, on the basis of these data, a three-dimensional image can be formed of the interior material of the body 1. If it is desired, as shown in FIG. 3a, to specifically examine a space 32 of the interior material, it is ensured that precisely this space is provided with the pulsed ultrasound. Here, in the example of FIG. 3a, the phase with which the ultrasonic transmitters 16.i.j. are controlled can be chosen so as to be equal. The sound will then propagate inside the substantially conical surface 34 shown in FIG. 3a and thus sufficiently fill the space 32 to examine the material 12 inside the space 32. In this manner, incidentally, a much larger area than the area 32 can be examined. However, when it is only intended to examine the area 32, it can be decided to choose the relative phases of the ultrasonic transmitters 16.i.j. such that the ultrasound propagates precisely to that area 32. This is indicated by the conical surface designated by reference numeral 36. The result is that the space 32 is filled with ultrasound having a higher energy density than when the ultrasonic transmitters are all controlled with an equal phase. Using the ultrasonic transmitters, an ultrasound beam is generated, as it were, which is specifically directed to (and converges in the direction of) the space 32 of which it is desired that it be examined. Completely analogous to what has been described hereinabove, then, reflections and/or diffractions of the transmitted ultrasound can be received using the ultrasonic receivers 16.i.j., while it can then be determined using the inverse wave field extrapolation where the virtual sources which have caused the respective reflections or diffractions are located. Thus, by variation of the relative phases of the ultrasonic transmitters, the ultrasound beam 36 can successively be directed into different directions for examining mutually different spaces 32 of the interior material of the body 1. Thus, the larger space 36 can be scanned using the beam 36. The receiving signals corresponding with a particular direction of a beam can then be processed on the basis of inverse wave field extrapolation as described hereinabove. Also, the beam can thus converge or diverge or, conversely, not converge or diverge, as desired. Here, it is further possible to process the receiving signals of different beams according to inverse wave field extrapolation. Per beam, an inverse wave field extrapolation can then be carried out, after which the results thus obtained per beam are processed in combination with each other for enhancing the accuracy. This is because, if the successive beams partly overlap, the same virtual sources will be found in two or more beams. It is also possible to process receiving signals from differently directed beams coming from transmitters at the same position in combination according to the principle of inverse wave field extrapolation. Different physical experiments are then combined. In addition, if the beams have mutually different directions, a larger area can be examined than if only one beam could be if the beams have mutually different directions used for examination. Precisely at those positions where the beams do not overlap, an area is then covered which cannot be covered by one of the beams at a time.

So, here it holds true that the ultrasound is supplied to the object such that a space comprising the interior material to be examined is scanned with an ultrasonic beam, while the receiving signals of reflections of the ultrasound from the completely scanned space are processed to determine, according to the principle of inverse wave extrapolation, where in the interior material of the object reflections of the ultrasound occur. Here, in this example, the response corresponding to a particular beam direction is used for tracing back the measured wave field to the above-mentioned position of the virtual sources on the basis of the inverse wave field extrapolation. Thus, per beam direction, of a part of the space, the positions of the virtual sources are determined. Then, the results of the positions of virtual sources determined for other parts of the space on the basis of a different direction of the beam can also be determined in order to map the position of the virtual sources of the whole space.

It is by no means necessary that the ultrasonic receivers 16.i.j. are each also designed as an ultrasonic transmitter. In the example of FIG. 3a, for instance, the ultrasonic receivers 16.i.j. may be designed as ultrasonic transmitters only. The apparatus may then further be provided with at least one ultrasonic transmitter 40. In this example, the body 1 is included between the ultrasonic receivers 16.i.j. on the one side and the transmitter 40 on the other side. Completely analogous to what has been discussed hereinabove, pulsed ultrasound is supplied to the body 1 using the transmitter 40.

The ultrasound will propagate through the interior material and diffraction and/or reflection will occur when the ultrasound passes or hits a transition in the material. Again, this diffraction and/or reflection can be considered a new virtual source whose sound energy in turn propagates through the material. Using the ultrasonic receivers 16.i.j., the sound energy of these new virtual sources is received. The received energy is recorded for a certain period using the ultrasonic receivers 16.i.j. Each of these receivers receives a response if possible. Completely analogous to what has been discussed hereinabove, on the basis of inverse wave field extrapolation, the detected wave field can be traced back to the position where it came from, namely the position of the virtual sources. This process of tracing back the measured wave field, the inverse wave field extrapolation, again gives the position, magnitude, shape and nature of the virtual sources as a result. All this can then be imaged as discussed hereinabove. If use is made of the transmitter 40, this is in effect a transmission system.

So, in this example, one separate transmitter 40 is involved. Of course, the transmitter 40 can be replaced by a plurality of transmitters 40 which are, for instance, arranged relative to each other according to the pattern of the receivers 16.i.j. These ultrasonic transmitters may also be located on an upper side 42 or a lower side 44 of the body 1. Then, it is also possible to concentrate the ultrasound transmitted by the transmitters in the space 32 or in the larger space 36 as desired, all this depending on the direction and shape of the beam of the ultrasound generated using the ultrasonic transmitters 40. Such variants are also understood to be within the framework of the invention.

In the apparatus according to FIG. 1, it is also possible, for instance, to activate the transmitters 16.i not simultaneously but consecutively. If ultrasound is transmitted with the transmitter 16.i, then the reflections and/or diffractions are received using the corresponding receiver 16.i. This experiment is repeatedly carried out for all transmitter and receiver elements 16.i (i=1, 2, 3, . . . , n). Also, the transmitter and receiver elements are moved in the radial direction so that, at different points in time, the transmitter and receiver elements are distributed in two dimensions of the outer surface and so that receiving signals are obtained corresponding with receiver elements distributed in two dimensions of the outer surface. These receiving signals can in turn be processed in combination according to the principle of inverse wave field extrapolation.

Completely analogous to what has been discussed hereinabove, the transmitters 16.i.j. can be activated successively. If ultrasound is transmitted with the transmitter 16.i.j., then the reflections and/or diffractions are received using, for instance, the corresponding receiver 16.i.j. This experiment is carried out repeatedly for all transmitter and receiver elements 16.i.j.(i=1, 2, 3, . . . ,n; j=1, 2, 3, . . . , m). Thus, receiving signals are obtained corresponding with receiver elements distributed in two dimensions of the outer surface. These receiving signals can in turn be processed in combination according to the principle of inverse wave field extrapolation. According to this method, however, n*m physical experiments are carried out. In the method described with reference to FIG. 2 where all transmitters were activated simultaneously, only one physical experiment was involved, however. This also holds true for the method of FIG. 3 where use is made of only one single transmitter 40. Therefore, the invention is not limited to supplying ultrasound to the interior material in one particular manner. What is important is that receiving signals are obtained corresponding with receivers which are distributed in two dimensions of the outer surface of the object, at different points in time or not. The receiving signals thus obtained are then processed in combination according to the principle of inverse wave field extrapolation.

It is noted that, for each of the embodiments described hereinabove, it holds true that the sound can be transmitted in the form of transversal waves and/or compression waves as desired. In the case that the object to be examined is a metal object, generally either transversal waves or compression waves will be used. In the case that the object is a human body, preferably, use will only be made of compression waves because precisely compression waves can propagate well in the body due to the properties of the human body.

The number of ultrasonic receivers n used in the apparatus according to FIG. 1a may vary. A practical value is, for instance, 64, but other values are also possible. In the apparatus according to FIGS. 2 and 3, n and m may, for instance, each have the value of 64 as well. However, other numbers are also possible. In the apparatus according to FIGS. 1a, 1b, 2a, 2b, the transmitters 16.i; 16.i.j. will also generally be controlled in phase. However, it is also possible, in a manner known per se as discussed in relation to FIG. 3, to relatively vary the phase of the transmitters for generating a beam of ultrasound whose direction and shape (diverging, converging, or, conversely, not diverging or converging) can be set by the phase variations. The pulse repetition frequency with which the ultrasound is transmitted may, for instance, be higher than 25 Hz. It is also possible that the frequency (i.e. the wavelength) of the ultrasound is varied between a low and a high frequency according to, for instance, the shape of a sawtooth, while not the time when a signal comes from a virtual source is determinative for the position of the virtual source, as is the case with an ultrasound wave transmitted in a pulse manner, but the magnitude of the received frequency. Such variants are understood to be within the framework of the invention.

The invention claimed is:

1. A method for examining the interior material of an object from a surface of an object, such as a pipeline or a human body, using ultrasound having a frequency of at least 100 KHz, wherein the ultrasound is supplied to the interior material of the object, characterized in that reflections and/or diffractions of the ultrasound from the interior material of the object are received using ultrasonic receivers which are acoustically coupled to the surface of the object at positions which are distributed in two dimensions of the surface of the object, at different points in time or not, wherein, with each of the ultrasonic receivers, a receiving signal is generated, wherein the receiving signals are processed in combination in order to determine, according to the principle of inverse wave field extrapolation, where in the interior material of the object reflections and/or diffractions occur.

2. A method according to claim 1, characterized in that the ultrasonic receivers are arranged relative to each other according to a unidimensional array, wherein the unidimensional array is moved along the surface in a known manner for obtaining receiving signals coming from the ultrasonic receivers distributed in two dimensions over the surface.

3. A method according to claim 1, characterized in that the ultrasonic receivers are arranged relative to each other according to a two-dimensional array.

4. A method according to claim 1, characterized in that the ultrasound is supplied to the object such that a space comprising the interior material to be examined is completely filled with the ultrasound.

5. A method according to claim 4, characterized in that a three-dimensional image of the material in the space is imaged on a display.

6. A method according to claim 1, characterized in that the ultrasound is supplied to the object such that a space comprising the interior material to be examined is scanned with an ultrasound beam, wherein the receiving signals of reflections and/or diffractions of the ultrasound from the completely scanned space are processed in order to determine, according to the principle of inverse wave field extrapolation, where in the interior material of the object reflections of the ultrasound occur.

7. A method according to claim 1, characterized in that it is determined, according to the principle of inverse wave field extrapolation, in which direction said reflections and/or diffractions occur.

8. A method according to claim 1, characterized in that the ultrasound is supplied to the object in a pulsed manner.

9. A method according to claim 1, characterized in that the ultrasound is supplied to the object using ultrasonic feelers, which ultrasonic feelers also form ultrasonic receivers for receiving the reflections and/or diffractions.

10. A method according to claim 1, characterized in that the ultrasound is supplied to the object using at least one ultrasonic transmitter, which ultrasonic transmitter differs from the ultrasonic feelers.

11. A method according to claim 1, characterized in that the at least one ultrasonic transmitter and the ultrasonic receivers are arranged relative to each other such that a transmission of the ultrasound through the interior of the object is measured as well.

12. A method according to claim 1, characterized in that the receiving signals are processed in real time.

13. A method according to claim 1, characterized in that the processing of the receiving signals is carried out such that the result of the processing can be imaged on a display.

14. A method according to claim 13, characterized in that a three-dimensional image of at least a part of the interior material of the object is imaged on the display.

15. A method according to claim 1, characterized in that a weld of a pipeline is examined.

16. A method according to claim 1, characterized in that a wall of a pipeline is examined.

17. A method according to claim 1, characterized in that a human body is examined.

18. A system for examining the interior material of an object, such as a pipeline or a human body, from a surface of an object using ultrasound having a frequency of at least 100 KHz, wherein the system is provided with at least one transmitter for supplying the ultrasound to the interior material of the object, a plurality of ultrasonic receivers for receiving reflections and/or diffractions of the ultrasound from the interior material of the object, and signal-processing means for processing receiving signals coming from the respective ultrasonic receivers, characterized in that the system is arranged such that, during use, the ultrasonic receivers are acoustically coupled to the surface of the object at positions which are distributed in two dimensions of the surface of the object, at different points in time or not, wherein, during use, a receiving signal is generated with each of the ultrasonic receivers, wherein the signal-processing means are arranged to process receiving signals coming from the ultrasonic receivers in combination according to the principle of inverse wave extrapolation in order to determine where in the interior material of the object reflections and/or diffractions of the ultrasound occur.

19. A system according to claim 18, characterized in that the ultrasonic receivers are arranged relative to each other according to a unidimensional array, wherein the system is arranged to move the unidimensional array along the surface during use for obtaining receiving signals coming from the ultrasonic receivers which are distributed in two dimensions over the surface.

20. A system according to claim 18, characterized in that the ultrasonic receivers are arranged relative to each other according to a two-dimensional array.

21. A system according to claim 18, characterized in that the system is arranged to supply the ultrasound to the object during use such that a space comprising the interior material to be examined is completely filled with the ultrasound.

22. A system according to claim 21, characterized in that the system is arranged to image a three-dimensional image of the material in the space on a display.

23. A system according to claim 18, characterized in that the system is arranged to supply the ultrasound to the object during use such that a space comprising the interior material to be examined is scanned with an ultrasound beam, wherein the receiving signals of reflections and/or diffractions of the ultrasound from the completely scanned space are processed in order to the determine, according to the principle of inverse wave extrapolation, where in the interior material of the object reflections and/or diffractions of the ultrasound occur.

24. A system according to claim 18, characterized in that the signal-processing means are arranged to determine, according to the principle of inverse wave extrapolation, in which direction said reflections and/or diffractions occur.

25. A system according to claim 18, characterized in that the system is arranged to supply the ultrasound to the object in a pulsed manner.

26. A system according to claim 18, characterized in that the system is provided with ultrasonic feelers which can each function as the at least one transmitter as well as one of the receivers.

27. A system according to claim 18, characterized in that the at least one transmitter on the one hand and the receivers on the other hand are accommodated in mutually different housings.

28. A system according to claim 18, characterized in that the ultrasonic transmitter and the ultrasonic receivers are arranged relative to each other such that, during use, the transmission of the ultrasound through the interior of the object is measured as well.

29. A system according to claim 18, characterized in that the system is arranged to process the receiving signals in real time using the signal-processing means.

30. A system according to claim 18, characterized in that the system is further provided with a display for imaging the result of the receiving signals processed by the signal-processing means.

31. A system according to claim 30, characterized in that the system is arranged to image a three-dimensional image of at least a part of the interior material of the object on the display.

* * * * *